(12) United States Patent
Coelho Tsou et al.

(10) Patent No.: US 8,487,152 B2
(45) Date of Patent: Jul. 16, 2013

(54) PROCESS FOR CONVERTING NATURAL GAS TO AROMATICS WITH ELECTROCHEMICAL REMOVAL OF HYDROGEN TO GENERATE ELECTRICAL POWER AND OBTAIN HYDROGEN

(75) Inventors: Joana Coelho Tsou, Heidelberg (DE); Alexander Panchenko, Ludwigshafen (DE); Annebart Engbert Wentink, Mannheim (DE); Sebastian Ahrens, Wiesloch (DE); Thomas Heidemann, Viernheim (DE)

(73) Assignee: BASF SE, Ludwigshafen (DE)

( * ) Notice: Subject to any disclaimer, the term of this patent is extended or adjusted under 35 U.S.C. 154(b) by 154 days.

(21) Appl. No.: 13/202,427

(22) PCT Filed: Mar. 30, 2010

(86) PCT No.: PCT/EP2010/054155
§ 371 (c)(1),
(2), (4) Date: Aug. 19, 2011

(87) PCT Pub. No.: WO2010/115768
PCT Pub. Date: Oct. 14, 2010

(65) Prior Publication Data
US 2011/0303550 A1  Dec. 15, 2011

(30) Foreign Application Priority Data

Apr. 6, 2009  (EP) .................................... 09157397

(51) Int. Cl.
*C07C 2/76* (2006.01)
*C07C 2/42* (2006.01)

(52) U.S. Cl.
USPC ............ 585/407; 585/408; 585/818; 585/943

(58) Field of Classification Search
USPC .................................. 585/407, 408, 818, 943
See application file for complete search history.

(56) References Cited

U.S. PATENT DOCUMENTS

| 7,019,184 | B2 | 3/2006 | Allison et al. |
| 2003/0144565 | A1 | 7/2003 | Allison et al. |
| 2011/0060176 | A1 | 3/2011 | Kiesslich et al. |
| 2011/0108432 | A1 | 5/2011 | Malkowsky et al. |
| 2011/0124933 | A1 | 5/2011 | Kiesslich et al. |

FOREIGN PATENT DOCUMENTS

| WO | 03 084905 | 10/2003 |
| WO | 2009 124902 | 10/2009 |

OTHER PUBLICATIONS

U.S. Appl. No. 13/393,837, filed Mar. 2, 2012, Schneider, et al.
Solymosi, F. et al., "Conversion of Ethane Into Benzene on $Mo_2C$/ZSM-5 Catalyst", Applied Catalysis A: General, vol. 166, No. 1, pp. 225-235, XP023613553, (Jan. 2, 1998).
Wang, D. et al., "Characterization of a Mo/ZSM-5 Catalyst for the Conversion of Methane to Benzene", Journal of Catalysis, vol. 169, pp. 347-358, (1997).
Stookey, D. J., "Membranes: Gas-Separation Applications", Ullmann's Encyclopedia of Industrial Chemistry, pp. 1-12, (2005).
International Search Report Issued Sep. 3, 2010 in PCT/EP10/054155 filed Mar. 30, 2010.
U.S. Appl. No. 13/260,083, filed Sep. 23, 2011, Coelho Tsou, et al.
U.S. Appl. No. 13/256,536, filed Sep. 14, 2011, Tsou, et al.
U.S. Appl. No. 13/259,863, filed Sep. 23, 2011, Coelho Tsou, et al.
U.S. Appl. No. 13/186,592, filed Jul. 20, 2011, Schneider, et al.
U.S. Appl. No. 13/383,014, filed Jan. 9, 2012, Kubanek, et al.
U.S. Appl. No. 13/383,321, filed Jan. 10, 2012, Kubanek, et al.

*Primary Examiner* — Thuan D Dang
(74) *Attorney, Agent, or Firm* — Oblon, Spivak, McClelland, Maier & Neustadt, L.L.P.

(57) ABSTRACT

The present invention relates to a process for converting aliphatic hydrocarbons having 1 to 4 carbon atoms to aromatic hydrocarbons, comprising the steps of:
a) converting a reactant stream E which comprises at least one aliphatic hydrocarbon having 1 to 4 carbon atoms in the presence of a catalyst under nonoxidative conditions to a product stream P comprising aromatic hydrocarbons and hydrogen, and
b) electrochemically removing at least some of the hydrogen formed in the conversion from the product stream P by means of a gas-tight membrane-electrode assembly which has at least one selectively proton-conducting membrane and, on each side of the membrane, at least one electrode catalyst, at least some of the hydrogen being oxidized to protons over the anode catalyst on the retentate side of the membrane, and the protons, after passing through the membrane, on the permeate side over the cathode catalyst, are partly, in
b1) reduced to hydrogen with application of a voltage, and partly, in
b2) reacted with oxygen to give water to generate electrical power, the oxygen originating from an oxygen-comprising stream O which is contacted with the permeate side of the membrane.

15 Claims, No Drawings

PROCESS FOR CONVERTING NATURAL GAS TO AROMATICS WITH ELECTROCHEMICAL REMOVAL OF HYDROGEN TO GENERATE ELECTRICAL POWER AND OBTAIN HYDROGEN

The present invention relates to a process for converting aliphatic hydrocarbons having 1 to 4 carbon atoms to aromatic hydrocarbons in the presence of a catalyst under nonoxidative conditions, wherein at least some of the hydrogen formed in the conversion is removed electrochemically by means of a membrane-electrode assembly. On the retentate side of the membrane, at least some of the hydrogen is oxidized to protons. After passing through the membrane, on the permeate side, some of the protons are reduced to hydrogen with application of a voltage, and the rest are reacted with oxygen to give water to generate electrical power. The oxygen originates from an oxygen-comprising stream O which is contacted with the permeate side of the membrane.

Aromatic hydrocarbons such as benzene, toluene, ethylbenzene, styrene, xylene and naphthalene constitute important intermediates in the chemical industry, demand for which continues to rise. In general, they are obtained by catalytic reforming from naphtha, which is in turn obtained from mineral oil. Recent studies show that global mineral oil reservoirs are more limited compared to the natural gas reservoirs. Therefore, the preparation of aromatic hydrocarbons from reactants which can be obtained from natural gas is an alternative which is now also of economic interest. The main component of natural gas is typically methane.

One possible reaction route for obtaining aromatics from aliphatics is that of nonoxidative dehydroaromatization (DHAM). The reaction is effected here under nonoxidative conditions, especially with exclusion of oxygen. In DHAM, a dehydrogenation and cyclization of the aliphatics to give the corresponding aromatics with release of hydrogen takes place. This forms 1 mol of benzene and 9 mol of hydrogen from 6 mol of methane.

Thermodynamic considerations show that the conversion is limited by the equilibrium position (D. Wang, J. H. Lunsford and M. P. Rosynek, "Characterization of a Mo/ZSM-5 catalyst for the conversion of methane to benzene", Journal of Catalysis 169, 347-358 (1997)). Calculations taking account of the methane, benzene, naphthalene and hydrogen components show that the equilibrium conversions for the isothermal conversion of methane to benzene (and naphthalene) decrease with rising pressure and falling temperature; for example, the equilibrium conversion at 1 bar and 750° C. is about 17%.

In order to efficiently utilize the methane unconverted in the reaction, i.e. to use it again for DHAM, a majority of the $H_2$ present in the reaction output should be removed, since the $H_2$ otherwise shifts the reaction equilibrium unfavorably in the direction of methane, thus lowering the yield of aromatic hydrocarbons.

A process for DHAM of hydrocarbons, especially of natural gas, with removal of the $H_2$ and of the aromatic hydrocarbons from the product gas and recycling of the residual product gas into the reaction zone, and the reconversion of the product gas after removal of the hydrogen and without preceding removal of the aromatic hydrocarbons in a further reaction stage, is described in U.S. Pat. No. 7,019,184 B2. Methods mentioned for removal of the $H_2$ are hydrogen-selective membranes and pressure-swing adsorption. The hydrogen removed can be used for power generation, for example in a combustion chamber or in a fuel cell.

In the case of hydrogen removal by means of a selectively hydrogen-pervious membrane, the hydrogen migrates as an $H_2$ molecule through the membrane. The diffusion rate depends on the difference in partial hydrogen pressure between the retentate and permeate sides of the membrane. This can in principle be influenced by three different methods: 1) compression of the feed gas, which increases the partial pressure, 2) generating a vacuum on the permeate side or 3) using a sweep gas on the permeate side, which lowers the partial pressure of the hydrogen. These methods are either mechanically demanding (options 1) and 2)) or require the separation of the sweep gas from the hydrogen. In addition, the corresponding apparatuses for compression and expansion of the gas mixture must be present. For kinetic reasons, a certain proportion of the hydrogen always remains in the retentate. For example, the permeate of a $H_2/CH_4$ mixture, which is obtained by means of a hydrogen-pervious polymer membrane, typically comprises 1 molecule of $CH_4$ per 10 molecules of $H_2$. In the case of a Pd membrane, which is selectively hydrogen-pervious from about 200° C. and reaches its optimal separation capacity at 400° C. to 500° C., the permeate typically comprises 1 molecule of $CH_4$ per 200 molecules of $H_2$.

In pressure-swing adsorption, an adsorbent is contacted cyclically with the hydrogenous stream in a first phase, and all components except hydrogen are retained by adsorption. In a second phase, these components are desorbed again by reduced pressure. This is a technically very complicated process, in which adsorbents have to be used and a hydrogen-comprising waste stream arises, the hydrogen content of which can be more than 40%; see Ullmann's Encyclopedia of Industrial Chemistry, Membranes: Gas Separation-Applications, D. B. Strooky, Elah Strategies, p. 6, Chesterfield, Mo., USA, 2005 Wiley-VCH Verlag, Weinheim.

In addition to pressure-swing adsorption and the use of selectively hydrogen-pervious membranes, the use of a "cold box" is a customary process for removing hydrogen from gas mixtures.

In hydrogen removal by means of a cold box, the gas mixture is cooled under pressures of 30 to 50 bar to about −150° C. to −190° C. The generation of these low temperatures is costly. If the mixture freed of hydrogen is to be used again in a reaction, it also has to be heated again to the appropriate reaction temperature, for example to 600 to 1000° C. for the dehydroaromatization.

The removal of hydrogen from a mixture of hydrogen and methane is described by B. Ibeh et al. (International Journal of Hydrogen Energy 32 (2007) pages 908-914). The starting point thereof was to study the suitability of natural gas as a carrier gas for the transport of hydrogen through the already existing infrastructure for natural gas transport, in which case the hydrogen, after being transported together with the natural gas, has to be removed again therefrom. B. Ibeh et al. used a fuel cell with a single proton exchange membrane and Pt or Pt/Ru anode electrocatalysts to remove hydrogen from hydrogen-methane mixtures. Hydrogen-methane mixtures were supplied to the fuel cell at atmospheric pressure and temperatures between 20 and 70° C.

It is an object of the present invention to provide a process for obtaining aromatic hydrocarbons from aliphatic hydrocarbons having 1 to 4 carbon atoms, which does not have the disadvantages known from the prior art processes. The aliphatic hydrocarbons used, just like the by-products obtained in the conversion, should be utilized efficiently. The process should have a very favorable energy balance and very low apparatus complexity.

The object is achieved in accordance with the invention by the process for converting aliphatic hydrocarbons having 1 to 4 carbon atoms to aromatic hydrocarbons, comprising the steps of:

a) converting a reactant stream E which comprises at least one aliphatic hydrocarbon having 1 to 4 carbon atoms in the presence of a catalyst under nonoxidative conditions to a product stream P comprising aromatic hydrocarbons and hydrogen, and b) electrochemically removing at least some of the hydrogen formed in the conversion from the product stream P by means of a gas-tight membrane-electrode assembly which has at least one selectively proton-conducting membrane and, on each side of the membrane, at least one electrode catalyst, at least some of the hydrogen being oxidized to protons over the anode catalyst on the retentate side of the membrane, and the protons, after passing through the membrane, on the permeate side over the cathode catalyst, are partly, in b1) reduced to hydrogen with application of a voltage, and partly, in b2) reacted with oxygen to give water to generate electrical power, the oxygen originating from an oxygen-comprising stream O which is contacted with the permeate side of the membrane.

One advantage of the process according to the invention is the electrochemical removal of the hydrogen formed from the product stream P. The driving force of the electrochemical hydrogen removal is the potential difference between the two sides of the membrane. Since the removal is not, as in the case of the customarily used hydrogen-selective membranes, dependent on the difference in partial hydrogen pressure between the two sides of the membrane, the hydrogen removal can be performed at very much lower pressures and pressure differences, preferably completely dispensing with a pressure difference imposed from the outside, and especially at the same pressure on the permeate and retentate sides. This significantly reduces the mechanical stress on the membrane, which, among other effects, increases the long-term stability thereof and enlarges the selection of materials useful for the membrane.

This also offers the possibility of performing the removal of the hydrogen at lower pressures than in the case of conventional membranes, and possesses the advantage that the overall process, i.e. the DHAM and the workup of the product stream P, can be performed at similar pressures. It is thus possible to dispense with complex apparatus for compressing and expanding the gas streams.

The electrochemical removal can be performed at high temperatures compared to the removal of the hydrogen by means of a cold box. The temperatures for the electrochemical removal of the hydrogen are typically room temperature or higher. The aromatic hydrocarbons which form in the conversion are typically, after cooling the product stream to temperatures below the boiling point of benzene, scrubbed out and removed by means of a gas-liquid separator. Since the electrochemical hydrogen removal can also be performed above the temperatures required here, the product stream P need not be cooled to a greater degree than is necessary for the removal of the aromatic hydrocarbons. Compared to the cold box, cooling steps and the apparatus required therefore are dispensed with. In the case of recycling of the product stream P comprising unconverted $C_1$-$C_4$-aliphatics into the conversion zone after removal of the hydrogen and of the aromatic hydrocarbons, the recycled product stream P has to be heated to a significantly lesser degree than in the case of removal of the hydrogen by means of a cold box. This saves energy.

Pd membranes are less suitable for removing the hydrogen in the present process since they begin to become hydrogen-pervious from about 200° C., such that only very low flow rates through the membranes are achieved at these temperatures. At the optimal operating temperature of about 400° C. to 500° C., however, undesired side reactions of the aliphatics present in the product stream P to be separated can take place over the Pd membranes, which lead to relatively rapid coking of the Pd membranes and to a correspondingly high requirement for regeneration.

The electrochemical removal of the hydrogen is significantly more effective compared to the removal by means of conventional hydrogen-selective membranes; for the same separating performance, it is therefore possible to reduce the membrane area required, or, for the same membrane area, to remove significantly more hydrogen, such that the hydrogen content remaining in the recycled product stream P is significantly lower. Overall, the process according to the invention is therefore associated with lower apparatus complexity.

Component stage b2) has the particular advantage of combining the electrochemical removal of the hydrogen formed from the product stream P with the simultaneous generation of electrical power.

In this case, the hydrogen is not, as known from the prior art, first removed and then fed as hydrogen to a power-generating process such as an external fuel cell or gas turbine, but the power is instead generated already in the course of removal. Compared to the processes known from the prior art, depending on the point of view, a separating apparatus or a unit for power generation from the hydrogen formed and the associated energy and substance losses are eliminated.

A very particularly advantageous aspect of the process according to the invention is the combination of component steps b1) and b2), since the power generated in component step b2) can be used directly to reduce the hydrogen protons in component step b1). How much hydrogen is removed in each case after component steps b1) and b2) can be adjusted as desired, according to whether more hydrogen or power is to be generated.

The process according to the invention thus provides economically viable utilization of the reactants used with simultaneously flexible production of valuable aromatic hydrocarbons, hydrogen and electrical power.

The invention is described in detail hereinafter.

The conversion of the reactant stream E to a product stream P takes place in the presence of a catalyst under nonoxidative conditions.

According to the present invention, "nonoxidative" means, in relation to the DHAM, that the concentration of oxidizing agents such as oxygen or nitrogen oxides in the reactant stream E is below 5% by weight, preferably below 1% by weight, more preferably below 0.1% by weight. Most preferably, the reactant stream E is free of oxygen. Likewise particularly preferred is a concentration of oxidizing agents in the reactant stream E which is equal to or less than the concentration of oxidizing agents in the source from which the $C_1$-$C_4$-aliphatics originate.

According to the invention, reactant stream E comprises at least one aliphatic having 1 to 4 carbon atoms. These aliphatics include, for example, methane, ethane, propane, n-butane, i-butane, ethene, propene, 1- and 2-butene, isobutene. In one embodiment of the invention, the reactant stream E comprises at least 50 mol %, preferably at least 60 mol %, more preferably at least 70 mol %, exceptionally preferably at least 80 mol %, especially at least 90 mol %, of $C_1$-$C_4$-aliphatics.

Among the aliphatics, particular preference is given to using the saturated alkanes; in that case, reactant stream E comprises preferably at least 50 mol %, preferably at least 60 mol %, more preferably at least 70 mol %, exceptionally preferably at least 80 mol %, especially at least 90 mol %, of alkanes having 1 to 4 carbon atoms.

Among the alkanes, methane and ethane are preferred, especially methane. In this embodiment of the present invention, reactant stream E comprises preferably at least 50 mol %, preferably at least 60 mol %, more preferably at least 70 mol %, exceptionally preferably at least 80 mol %, especially at least 90 mol %, of methane.

The source used for the $C_1$-$C_4$-aliphatics is preferably natural gas. The typical composition of natural gas is as follows: 75 to 99 mol % of methane, 0.01 to 15 mol % of ethane, 0.01 to 10 mol % of propane, up to 6 mol % of butane, up to 30 mol % of carbon dioxide, up to 30 mol % of hydrogen sulfide, up to 15 mol % of nitrogen and up to 5 mol % of helium. Before use in the process according to the invention, the natural gas can be purified and enriched by methods known to those skilled in the art. The purification includes, for example, the removal of any hydrogen sulfide or carbon dioxide present in the natural gas and of further compounds which are undesired in the subsequent process.

The $C_1$-$C_4$-aliphatics present in reactant stream E may also originate from other sources, for example may have originated in the course of crude oil refining. The $C_1$-$C_4$-aliphatics may also have been produced by renewable means (e.g. biogas) or synthetic means (e.g. Fischer-Tropsch synthesis).

If the $C_1$-$C_4$-aliphatic source used is biogas, reactant stream E may additionally also comprise ammonia, traces of lower alcohols and further additives typical of biogas.

In a further embodiment of the process according to the invention, the reactant stream E used may be LPG (liquid petroleum gas). In a further embodiment of the process according to the invention, the reactant stream E used may be LNG (liquefied natural gas).

It is additionally possible to add hydrogen, steam, carbon monoxide, carbon dioxide, nitrogen and one or more noble gases to reactant stream E.

In step a) of the process according to the invention, the conversion of reactant stream E takes place under nonoxidative conditions in the presence of a catalyst to a product stream P comprising aromatic hydrocarbons. This conversion is a dehydroaromatization, i.e. the $C_1$-$C_4$-aliphatics present in reactant stream E react with dehydrogenation and cyclization to give the corresponding aromatics, which releases hydrogen. According to the invention, the DHAM is performed in the presence of suitable catalysts. Generally, all catalysts which catalyze DHAM can be used in step a) of the process according to the invention. Typically, the DHAM catalysts comprise a porous support and at least one metal applied thereto. The support typically comprises a crystalline or amorphous inorganic compound.

According to the invention, the catalyst preferably comprises at least one metalosilicate as a support. Preference is given to using aluminum silicates as supports. Very particular preference is given in accordance with the invention to using zeolites as supports. Zeolites are aluminum silicates which are typically obtained in the sodium form when they are prepared. In the Na form, the excess negative charge which is present in the crystal lattice owing to the exchange of tetravalent silicon atoms for trivalent aluminum atoms is balanced by sodium ions. Instead of sodium alone, the zeolite may also comprise further alkali metal and/or alkaline earth metal ions to balance the charge. Preferably in accordance with the invention, the at least one zeolite present in the catalysts has a structure selected from the pentasil and MWW structure types and more preferably from the MFI, MEL, mixed MFI/MEL and MWW structure types. Very particular preference is given to using a zeolite of the ZSM-5 or MCM-22 type. The designations of the structure types of the zeolites correspond to the information in W. M. Meier, D. H. Olson and Ch. Baerlocher, "Atlas of Zeolite Structure Types", Elsevier, 3rd edition, Amsterdam 2001. The synthesis of the zeolites is known to those skilled in the art and can, for example, be carried out proceeding from alkali metal aluminate, alkali metal silicate and amorphous $SiO_2$ under hydrothermal conditions. In this synthesis, the type of channel systems formed in the zeolite can be controlled by means of organic template molecules, by means of the temperature and further experimental parameters.

In addition to Al, the zeolites may comprise further elements such as Ga, B, Fe or In.

Preference is given to using the zeolites which are used preferentially as supports in the H form or the ammonium form, in which the zeolites are also commercially available.

When they are converted from the Na form to the H form, the alkali metal and/or alkaline earth metal ions present in the zeolite are exchanged for protons. A customary process for converting the catalysts to the H form, which is preferred in accordance with the present invention, is a two-stage process in which the alkali metal and/or alkaline earth metal ions are first exchanged for ammonium ions. When the zeolite is heated to about 400 to 500° C., the ammonium ion decomposes to volatile ammonia and the proton remaining in the zeolite.

To this end, the zeolite is treated with an $NH_4$-containing mixture. The $NH_4$-containing component used in the $NH_4$-containing mixture is an ammonium salt selected from the group of ammonium chloride, ammonium carbonate, ammonium hydrogencarbonate, ammonium nitrate, ammonium phosphate, ammonium acetate, ammonium hydrogen-phosphate, ammonium dihydrogenphosphate, ammonium sulfate and ammonium hydrogensulfate. Preference is given to using ammonium nitrate as the $NH_4$-containing component.

The zeolite is treated with the $NH_4$-containing mixture by the known methods suitable for ammonium exchange of zeolites. These include, for example, impregnating, dipping or spraying the zeolite with an ammonium salt solution, the solution generally being employed in excess. The solvents used are preferably water and/or alcohols. The mixture comprises typically 1 to 20% by weight of the $NH_4$ component used. The treatment with the $NH_4$-containing mixture is performed typically over a period of several hours and at elevated temperatures. After the action of the $NH_4$-containing mixture on the zeolite, excess mixture can be removed and the zeolite can be washed. Subsequently, the zeolite is dried at 40 to 150° C. for several hours, typically 4 to 20 hours. This is followed by the calcination of the zeolite at temperatures of 300 to 700° C., preferably 350 to 650° C. and more preferably 500 to 600° C. The duration of the calcination is typically 2 to 24 hours, preferably 3 to 10 hours, more preferably 4 to 6 hours.

In a preferred embodiment of the present invention, the supports used are zeolites which have been treated again with an $NH_4$-containing mixture and then dried. The further treatment of the zeolites with the $NH_4$-containing mixture is effected according to the above description.

Commercially available zeolites in the H form have typically already passed through a first ammonium exchange by treatment with an $NH_4$-containing mixture with subsequent drying and calcination. Therefore, it is possible in accordance with the invention to use commercially purchased zeolites present in the H form as support a), but preference is given to subjecting them to another treatment with an $NH_4$-containing mixture and if appropriate to calcining them.

Typically, the DHAM catalyst comprises at least one metal. Typically, the metal is selected from groups 3 to 12 of the Periodic Table of the Elements (IUPAC). Preferably in accordance with the invention, the DHAM catalyst comprises at least one metal selected from transition metals of transition groups 5 to 11. The DHAM catalyst more preferably comprises at least one metal selected from the group of Mo, W, Mn, Tc, Re, Fe, Ru, Os, Co, Rh, Ir, Ni, Pd, Pt, Cu, Cr, Nb, Ta, Ag and Au. More particularly, the DHAM catalyst comprises at least one metal selected from the group of Mo, W, Re, Fe, Ru, Os, Co, Rh, Ir, Ni, Pd, Pt, Cu. Most preferably, the DHAM catalyst comprises at least one metal selected from the group of Mo, W and Re.

Likewise preferably in accordance with the invention, the DHAM catalyst comprises at least one metal as an active component and at least one further metal as a dopant. According to the invention, the active component is selected from Mo, W, Re, Ru, Os, Rh, Ir, Pd, Pt. According to the invention, the dopant is selected from the group of Cr, Mn, Fe, Co, Nb, Ta, Ni, Cu, V, Zn, Zr and Ga, preferably from the group of Fe, Co, Ni, Nb, Ta, Cu and Cr. According to the invention, the DHAM catalyst may comprise more than one metal as an active component and more than one metal as a dopant. These are each selected from the metals specified for the active component and the dopant. The catalyst preferably comprises a metal as the active component and one or two metals as dopants.

According to the invention, the at least one metal is applied to the support by wet chemical or dry chemical means, by the methods known to those skilled in the art.

In wet chemical methods, the metals are applied in the form of aqueous, organic or organic-aqueous solutions of their salts or complexes by impregnating the support with the corresponding solution. The solvent used may also be supercritical $CO_2$. The impregnation can be effected by the incipient wetness method, in which the porous volume of the support is filled by about the same volume of impregnation solution and—if appropriate after maturation—the support is dried. It is also possible to work with an excess of solution, in which case the volume of this solution is greater than the porous volume of the support. In this case, the support is mixed with the impregnation solution and stirred for a sufficiently long period. In addition, it is possible to spray the support with a solution of the appropriate metal compound. Other preparation methods known to those skilled in the art are also possible, such as precipitation of the metal compounds onto the support, spray application of a solution comprising metal compound, sol impregnation, etc. After the application of the at least one metal to the support, the catalyst is dried at about 80 to 130° C. under reduced pressure or under air, typically for 4 to 20 hours.

According to the invention, the at least one metal can also be applied by dry chemical methods, for example by depositing the metal carbonyls which are gaseous at higher temperatures, such as $Mo(CO)_6$, $W(CO)_6$ and $Re_2(CO)_{10}$, on the support from the gas phase. The deposition of the metal carbonyl compound is performed after the calcination of the support. It can also be mixed with the support in the form of a fine powder, for example as the carbide.

According to the invention, the catalyst comprises 0.1 to 20% by weight, preferably 0.2 to 15% by weight, more preferably 0.5 to 10% by weight, based in each case on the total weight of the catalyst, of the at least one metal. The catalyst may comprise only one metal; it may also comprise a mixture of two, three or more metals. The metals can be applied by wet chemical means together in one solution, or in different solutions in succession with drying steps between the individual applications. The metals can also be applied in mixed form, i.e. one portion by wet chemical means and another portion by dry chemical means. Between the applications of the metal compounds, calcination can be effected if required according to the above description.

According to the invention, the catalyst may comprise at least one metal from the group of the active components in conjunction with at least one metal selected from the group of the dopants. In this case, the concentration of the active component is 0.1 to 20% by weight, preferably 0.2 to 15% by weight, more preferably 0.5 to 10% by weight, based in each case on the total weight of the catalyst. In this case, the dopant is present in the catalyst, according to the invention, in a concentration of at least 0.1% by weight, preferably at least 0.2% by weight, most preferably at least 0.5% by weight, based on the total weight of the catalyst.

In a further preferred embodiment of the present invention, the catalyst is mixed with a binder. Suitable binders are the customary binders known to those skilled in the art, such as aluminum oxide- and/or Si-containing binders. Particular preference is given to Si-containing binders; especially suitable are tetraalkoxysilanes, polysiloxanes and colloidal $SiO_2$ sols.

According to the invention, addition of the binder is followed by a shaping step, in which the catalyst material is processed by processes known to those skilled in the art to shaped bodies. Examples of shaping processes include spraying of a suspension comprising the support a) and/or the catalyst material, spray-drying, tableting, pressing in the moist or dry state and extrusion. Two or more of these processes may also be combined. For the shaping, it is possible to add assistants such as pore formers and pasting agents, or else other additives known to those skilled in the art. Possible pasting agents are those compounds which lead to an improvement in the mixing, kneading and flow properties. In the context of the present invention, these are preferably organic, especially hydrophilic polymers, for example cellulose, cellulose derivatives such as methylcellulose, starch such as potato starch, wallpaper paste, acrylates, polyacrylates, polymethacrylates, polyvinyl alcohols, polyvinylpyrrolidone, polyisobutylene, polytetrahydrofuran, polyglycol ethers, fatty acid compounds, wax emulsions, water or mixtures of two or more of these compounds. Examples of pore formers in the context of the present invention include compounds which are dispersible, suspendable or emulsifiable in water or aqueous solvent mixtures, such compounds including polyalkylene oxides, polystyrene, polyacrylates, polymethacrylates, polyolefins, polyamides, polyesters, carbohydrates, cellulose, cellulose derivatives, for example methylcellulose, natural sugar fibers, pulp, graphite or mixtures of two or more of these compounds. Pore formers and/or pasting agents are, after the shaping, preferably removed from the resulting shaped body by at least one suitable drying and/or calcination step. The conditions required for this purpose can be selected analogously to the parameters described above for calcination and are known to those skilled in the art.

Especially for use as fluidized bed catalysts, the shaped catalyst bodies are produced by means of spray-drying.

The geometry of the catalysts obtainable in accordance with the invention may, for example, be spherical (hollow or solid), cylindrical (hollow or solid), annular, saddle-shaped, star-shaped, honeycomb-shaped or tablet-shaped. In addition, extrudates are useful, for example in strand form, trilobal form, quatrolobal form, star form or hollow cylindrical form. In addition, the catalyst material to be shaped can be extruded and calcined, and the extrudates thus obtained can be crushed and processed to spall or powder. The spall can be separated into different screen fractions.

In a preferred embodiment of the invention, the catalyst is used in the form of shaped bodies or spall.

In a further preferred embodiment, the catalyst is used in the form of powder. The catalyst powder may comprise binders, or else be free of binders.

When the inventive catalyst comprises a binder, it is present in a concentration of 5 to 80% by weight, based on the total weight of the catalyst, preferably 10 to 50% by weight, more preferably 10 to 30% by weight.

It may be advantageous to activate the catalyst used for dehydroaromatization of $C_1$-$C_4$-aliphatics before the actual reaction.

This activation can be effected with a $C_1$-$C_4$-alkane, for example ethane, propane, butane or a mixture thereof, preferably butane. The activation is carried out at a temperature of 250 to 850° C., preferably 350 to 650° C., and a pressure of 0.5 to 5 bar, preferably 0.5 to 2 bar. Typically, the GHSV (gas hourly space velocity) in the activation is 100 to 4000 $h^{-1}$, preferably 500 to 2000 $h^{-1}$.

However, it is also possible to carry out an activation by virtue of the reactant stream E already comprising the $C_1$-$C_4$-alkane, or a mixture thereof, per se, or by adding the $C_1$-$C_4$-alkane, or a mixture thereof, to the reactant stream E. The activation is carried out at a temperature of 250 to 650° C., preferably at 350 to 550° C., and a pressure of 0.5 to 5 bar, preferably 0.5 to 2 bar.

In a further embodiment, it is also possible additionally to add hydrogen to the $C_1$-$C_4$-alkane.

In a preferred embodiment of the present invention, the catalyst is activated with an $H_2$-comprising gas stream which may additionally comprise inert gases such as $N_2$, He, Ne and Ar.

According to the invention, the dehydroaromatization of $C_1$-$C_4$-aliphatics is performed in the presence of a catalyst at temperatures of 400 to 1000° C., preferably 500 to 900° C., more preferably 600 to 800° C., especially 700 to 800° C., at a pressure of 0.5 to 100 bar, preferably 1 to 30 bar, more preferably 1 to 10 bar, especially 1 to 5 bar. According to the present invention, the reaction is performed at a GHSV (gas hourly space velocity) of 100 to 10,000 $h^{-1}$, preferably 200 to 3000 $h^{-1}$.

The dehydroaromatization of $C_1$-$C_4$-aliphatics in step a) can in principle be carried out in all reactor types known from the prior art. A suitable reactor form is the fixed bed reactor, radial flow reactor, tubular reactor or tube bundle reactor. In these reactors, the catalyst is present as a fixed bed in one reaction tube or in a bundle of reaction tubes. The catalysts may likewise be used as a fluidized bed or moving bed in the corresponding reactor types suitable for this purpose, and the process according to the invention may be carried out with the catalysts present in such a form.

According to the invention, the catalyst may be used undiluted or mixed with inert material. The inert material used may be any material which behaves inertly, i.e. does not react, under the reaction conditions which exist in the reaction zones. Suitable inert materials are particularly the undoped support which is used for the catalyst, but also inert zeolites, aluminum oxide, silicon dioxide, etc. The particle size of the inert material is within the range of the size of the catalyst particles.

Preferably in accordance with the present invention, the undiluted catalyst or that mixed with inert material is present in the form of a fixed, moving or fluidized bed. The catalyst or the mixture of catalyst and inert material is more preferably present in the form of a fluidized bed.

In one embodiment of the invention, the catalyst used in the DHAM is regenerated regularly. The regeneration can be performed by the customary processes known to those skilled in the art. Preferably in accordance with the invention, the regeneration is performed under reducing conditions by means of a hydrogen-comprising gas stream.

The regeneration is performed at temperatures of 600° C. to 1000° C. and more preferably of 700° C. to 900° C., and pressures of 1 bar to 30 bar, preferably of 1 bar to 15 bar and more preferably of 1 to 10 bar.

According to the invention, the $C_1$-$C_4$-aliphatics are converted to aromatics with release of $H_2$. The product stream P therefore comprises at least one aromatic hydrocarbon selected from the group of benzene, toluene, ethylbenzene, styrene, xylene and naphthalene. It preferably comprises benzene and toluene. In addition, the product stream comprises unconverted $C_1$-$C_4$-aliphatics, hydrogen formed, and the inert gases present in the reactant stream E, such as $N_2$, He, Ne, Ar, substances added to the reactant stream E, such as $H_2$, and impurities which were already present in the reactant stream E.

In step b) of the process according to the invention, at least some of the hydrogen present in the product stream P is removed electrochemically by means of a gas-tight membrane-electrode assembly, and the hydrogen to be removed is transported through the membrane in the form of protons. The electrodes with the membrane arranged in between are referred to as membrane-electrode assembly (MEA). The product stream P is conducted along one side of the membrane. This side is referred to hereinafter as retentate side. The other side of the membrane is referred to hereinafter as permeate side. On this side, the hydrogen formed in component step b1) and the water formed in component step b2) are removed. According to the invention, the MEA has at least one selectively proton-conducting membrane. The membrane has at least one electrode catalyst on each side, the electrode catalyst present on the retentate side being referred to in the context of this description as the anode catalyst, and the electrode catalyst present on the permeate side as the cathode catalyst. On the retentate side, the hydrogen is oxidized over the anode catalyst to protons, which pass through the membrane and are partly reduced to hydrogen (b1)) over the cathode catalyst on the permeate side and partly reacted with oxygen to give water and generate electrical energy (b2)); in component step b2), to this end, an oxygen-comprising stream O is conducted along the permeate side and contacted with the membrane. In component step b1), electrical energy has to be expended for the transport of the protons through the membrane, and is supplied by applying a direct voltage to the two sides of the membrane by means of electrodes.

In order to ensure good contact of the membrane with the hydrogen present on the retentate side and good transport of the hydrogen removed or of the water away from the permeate side, the electrode layers are typically contacted with gas distributor layers. These are, for example, plates with a lattice-like surface structure composed of a system of fine channels or layers of porous material, such as nonwoven or woven fabric, or paper. The entirety of gas distributor layer and electrode layer is generally referred to as a gas diffusion electrode (GDE). By virtue of the gas distributor layer, the hydrogen to be removed is conducted close to the membrane and the anode catalyst on the retentate side, and the transport of the hydrogen formed or water away on the permeate side is facilitated.

According to the embodiment of the invention, the anode may simultaneously also serve as the anode catalyst, and the cathode simultaneously also as the cathode catalyst. However, it is also possible to use different materials in each case for the anode and the anode catalyst, or the cathode and the cathode catalyst.

To produce the electrodes, it is possible to use the customary materials known to those skilled in the art. For example, the electrodes may comprise Pt, Pd, Cu, Ni, Fe, Ru, Co, Cr, Fe, Mn, V, W, tungsten carbide, Mo, molybdenum carbide, Zr, Rh, Ag, Ir, Au, Re, Y, Nb, electrically conductive forms of carbon such as carbon black, graphite and nanotubes, and alloys and mixtures of the aforementioned elements.

The anode and the cathode may be produced from the same material or from different materials. The anode catalyst and the cathode catalyst may be selected from the same or different materials. Particularly preferred anode/cathode combinations are Pt/Pt, Pd/Pd, Pt/Pd, Pd/Pt, Ni/Ni, Fe/Fe and Ni/Pt.

The electrode catalyst materials used may be the customary compounds and elements which are known to those skilled in the art and can catalyze the dissociation of molecular hydrogen to atomic hydrogen, the oxidation of hydrogen to protons and the reduction of protons to hydrogen. Suitable examples are Pd, Pt, Cu, Ni, Fe, Ru, Co, Cr, Mn, V, W, tungsten carbide, Mo, molybdenum carbide, Zr, Rh, Ag, Ir, Au, Re, Y, Nb, and alloys and mixtures thereof, preference being given in accordance with the invention to Pd and Pt. The elements and compounds mentioned above as electrode catalyst materials may also be present in supported form, in which case preference is given to using carbon as the support.

In a preferred embodiment of the present invention, preference is given to using carbon as electrodes comprising conductive material. In this case, the carbon and an electrode catalyst are preferably applied to a porous support such as nonwoven or woven fabric, or paper. The carbon may be mixed with the catalyst, or first the carbon and then the catalyst may be applied.

In a further embodiment of the invention, the electrically conductive material used as the electrode and the electrode catalyst are applied directly to the membrane.

The membrane is preferably configured as a plate or as a tube, it being possible to use the customary membrane arrangements known from the prior art for separation of gas mixtures, for example tube bundle or insertable plate membranes.

The MEA used in accordance with the invention is gas-tight, i.e. it has virtually zero porosity through which gases in atomic or molecular form can pass from one side to the other side of the MEA, nor does it have any mechanisms by which the gases can be transported unselectively through the MEA, for example by adsorption, dissolution in the membrane, diffusion and desorption.

The imperviosity of the membrane-electrode assembly (MEA) can be ensured by a gas-tight membrane, by a gas-tight electrode and/or a gas-tight electrode catalyst. For instance, the gas-tight electrode used may, for example, be a thin metallic foil, for example a Pd, Pd—Ag or Pd—Cu foil.

The membrane used in accordance with the invention selectively conducts protons, which means more particularly that it is not electron-conductive. According to the invention, it is possible to use, for the membranes, all materials which are known to the person skilled in the art and from which proton-conducting membranes can be formed. These include, for example, the materials listed by J. W. Phair and S. P. S. Badwal in Ionics (2006) 12, pages 103-115. It is also possible in accordance with the invention to use selectively proton-conducting membranes as known from fuel cell technology.

For example, it is possible to use particular heteropolyacids such as $H_3Sb_3B_2O_{14}.10H_2O$, $H_2Ti_4O_9.12H_2O$ and $HSbP_2O_8.10H_2O$; acidic zirconium silicates, phosphates and phosphonates in layer structure, such as $K_2ZrSi_3O_9$, $K_2ZrSi_3O_9$, alpha-$Zr(HPO_4)_2.nH_2O$, gamma-$Zr(PO_4)$—$(H_2PO_4).2H_2O$, alpha- and gamma-zirconium sulfophenylphosphonate or sulfoarylphosphonate; unlayered oxide hydrates such as antimonic acid ($Sb_2O_5.2H_2O$), $V_2O_5.nH_2O$, $ZrO_2.nH_2O$, $SnO_2.nH_2O$ and $Ce(HPO_4)_2.nH_2O$. In addition, it is possible to use oxo acids and salts which comprise, for example, sulfate, selenate, phosphate, arsenate, nitrate groups, etc. Particularly suitable are oxoanion systems based on phosphates or complex heteropolyacids, such as polyphosphate glasses, aluminum polyphosphate, ammonium polyphosphate and polyphosphate compositions such as $NH_4PO_3/(NH_4)_2SiP_4O_{13}$ and $NH_4PO_3/TiP_2O_7$. In addition, oxidic materials are usable, such as brownmillerites, fluorites and phosphates with apatite structure, pyrochlore minerals and perovskites.

Perovskites have the empirical formula $AB_{1-x}M_xO_{3-y}$ where M is a trivalent rare earth element which serves for doping, and y denotes the oxygen deficiency in the perovskite oxide lattice. A can be selected, for example, from Mg, Ca, Sr and Ba. B may be selected, inter alia, from Ce, Zr and Ti. For A, B and M, it is also possible to independently select different elements from the particular groups.

In addition, it is possible to use structurally modified glasses, such as chalcogenide glasses, PbO—$SiO_2$, BaO—$SiO_2$ and CaO—$SiO_2$.

A further class of materials which are suitable for the production of gas-tight and selectively proton-conducting membranes is that of polymer membranes. Suitable polymers are sulfonated polyetheretherketones (S-PEEK), sulfonated polybenzimidazoles (S-PBI) and sulfonated fluorohydrocarbon polymers (NAFION®). In addition, it is possible to use perfluorinated polysulfonic acids, polymers based on styrene, poly(arylene ethers), polyimides and polyphosphazenes.

According to the invention, the materials used for the selectively proton-conducting membrane are preferably the aforementioned polymers and the compounds based on phosphates. Very particular preference is given to using membranes composed of polybenzimidazoles, especially MEAs based on polybenzimidazole and phosphoric acid, as sold, for example, under the Celtec-P® name by BASF SE.

In the case of use of polymer membranes, they are typically moistened by the presence of about 0.5 to 50% by volume of water on at least one side, but better on both sides, of the membrane. On the retentate side, the concentration can be adjusted by adding water to the reactant stream E, to the product stream P, to the reaction zone, or in the case of recycling of the product stream P which has been freed of $H_2$ and aromatics and already comprises a certain amount of water from its already completed passage through the process. On the permeate side too, the required water concentration is typically ensured by metered addition of water, but this is unnecessary in component step b2).

Preference is likewise given to using ceramic membranes.

Suitable proton-conducting ceramics are described, for example, in Solid State Ionics 125, (1999), 271-278; Journal of Power Sources 180, (2008), 15-22; Ionics 12, (2006), 103-115; Journal of Power Sources 179 (2008) 92-95; Journal of Power Sources 176 (2008) 122-127 and Electrochemistry Communications 10 (2008) 1005-1007.

Examples of proton-conducting ceramics and oxides are $SrCeO_3$, $BaCeO_3$, Yb:$SrCeO_3$, Nd:$BaCeO_3$, Gd:$BaCeO_3$, Sm:$BaCeO_3$, $BaCaNdO_9$, Y:$BaCeO_3$, Y:$BaZrCeO_3$, Pr-doped Y:$BaCeO_3$, Gd:$BaCeO_3$, $BaCe_{0.9}Y_{0.1}O_{2.95}$ (BYC), $SrCe_{0.95}Yb_{0.05}O_{3-\alpha}$, $BaCe_{0.9}Nd_{0.10}O_{3-\alpha}$, $CaZr_{0.96}In_{0.04}O_{3-\alpha}$, ($\alpha$ denotes the number of oxygen defect sites per formula unit of the oxide of the perovskite type); Sr-doped $La_3P_3O_9$, Sr-doped $LaPO_4$, $BaCe_{0.9}Y_{0.1}O_{3-\alpha}$ (BCY), $BaZr_{0.9}Y_{0.1}O_{3-\alpha}$ (BZY), $Ba_3Ca_{1.18}Nb_{1.82}O_{8.73}$ (BCN18), $(La_{1.95}Ca_{0.05})Zr_2O_{7-\alpha}$, $_{La2}Ce_2O_7$, $Eu_2Zr_2O_7$, $H_2S/(B_2S_3$ or $Ga_2S_3)/GeS_2$, $SiS_2$, $As_2S_3$ or CsI; $BaCe_{0.8}Gd_{0.2}O_{3-\alpha}$ (BCGO); Gd-doped $BaCeO_3$ such as $BaCe_{0.85}Y_{0.15}O_{3-\alpha}$ (BCY15) and $BaCe_{0.8}Sm_{0.2}O_{3-\alpha}$, $xAl_2O_3$ $(1-x)SiO_2$ (x=0.0-1.0), $SnP_2O_7$, $Sn_{1-x}In_xP_2O_7$ (x=0.0-0.2).

The removal of the hydrogen in step b) of the process according to the invention can be performed at temperatures of 20 to 1200° C., preferably of 20 to 800° C., more preferably of 20 to 500° C. and most preferably at 70 to 250° C. In the case of use of MEAs based on polybenzimidazole and phosphoric acid, the removal is preferably undertaken at 130° C. to 200° C.

The removal of the hydrogen in step b) of the process according to the invention is preferably undertaken at pressures of 0.5 to 10 bar, preferably of 1 to 6 bar, more preferably of 1 to 4 bar. In a preferred embodiment of the invention, the pressure difference between the retentate side and the permeate side of the membrane is less than 1 bar, preferably less than 0.5 bar, and there is more preferably no pressure difference.

According to the invention, the removal of the hydrogen in step b) is performed at voltages of 0.05 to 2000 mV, preferably of 100 to 1500 mV, more preferably of 100 to 900 mV and most preferably of 100 to 800 mV, relative to an RHE (hydrogen reference electrode).

The oxygen-comprising stream used in component step b2) comprises, in accordance with the invention, at least 15 mol %, preferably at least 20 mol %, of oxygen. In a preferred embodiment, air is used as the oxygen-comprising stream O, or oxygen-enriched air. The air is typically used in unpurified form.

The flow rate of the stream O is selected such that the amount of $O_2$, in stoichiometric terms, is 1 to 10 times, preferably 1.2 to 5 times and more preferably 1.5 to 2.5 times the amount of $H_2$.

According to the invention, in step b), at least some of the hydrogen formed in the DHAM is removed. Preferably at least 30%, more preferably at least 50%, more preferably at least 70% and even more preferably at least 95%, especially at least 98%, is removed.

The hydrogen obtained on the permeate side in component step b1) comprises at most 5 mol %, preferably at most 2 mol % and more preferably at most 1 mol % of aliphatics having 1 to 4 carbon atoms. In addition, the hydrogen, according to the selectively proton-conducting membrane used, may comprise up to 50% by volume, preferably up to 20% by volume, more preferably up to 5% by volume of water. The presence of water is required for some membrane types, for example in the case of particular polymer membranes to moisten the membrane.

According to the invention, the electrochemical removal of the hydrogen in step b) takes place outside the reaction zone in which step a) is performed.

The aromatic hydrocarbons present in the product stream P are removed by the processes known to those skilled in the art.

In one embodiment, the aromatic hydrocarbons formed are removed from the product stream P between steps a) and b). In a further embodiment of the invention, the aromatic hydrocarbons formed are removed from the product stream after step b).

In a particularly preferred embodiment of the invention, the product stream P, after removal of the aromatic hydrocarbons and of at least some of the hydrogen, is recycled into the process; the product stream P is either recycled to the reactant stream E or directly into the reaction zone for the DHAM. It is preferred in accordance with the invention that a maximum amount of hydrogen is removed before the recycling, since hydrogen shifts the reaction equilibrium to the side of the reactants in the DHAM. The product stream P recycled comprises preferably 0 to 2 mol %, preferentially 0 to 1 mol %, of hydrogen.

The above-described catalysts based on zeolites treated twice with $NH_3$ solution have, even without the addition of hydrogen to the reactant stream, which is customary in the prior art, a long lifetime and are therefore particularly suitable for use as DHAM catalysts in the recycling of the product stream P after removal of a maximum portion of the hydrogen present.

The hydrogen removed in component step b1) can also be dried before further use; this is performed especially when polymer membranes which have to be moistened are used in step b).

According to the invention, at least some of the hydrogen is removed in step b), part of it after each of component steps b1) and b2). This means that some of the hydrogen is removed as hydrogen, and the rest of the hydrogen as water to generate electrical energy. How much of the hydrogen present in the product stream P is removed after each of component steps b1) and b2) can be adjusted by the user as required. In a preferred embodiment of the invention, at least sufficient hydrogen is removed in b2) that the stream obtained is sufficient to cover the energy demand for the hydrogen removal in component step b1), i.e. the power required for the removal of the hydrogen in component step b1) is generated by component step b2).

The removal of the hydrogen from the product stream P is preferably performed with spatial separation, since, when oxygen is present on the permeate side, the protons typically react directly to give hydrogen. The product stream P can, for example, be passed successively first along an MEA which is in contact with a stream O on the permeate side, such that some of the hydrogen is removed as water. Subsequently, the product stream P is conducted along an MEA to which a voltage is applied, such that the hydrogen is removed as hydrogen. The spatial separation between the two component steps b1) and b2) may also consist in the fact that the product stream P is passed through between two membranes, for example opposite one another, one of which is in contact with a stream O on the permeate side, and a voltage is applied to the other.

EXAMPLES

Examples 1 and 2 demonstrate the removal of the hydrogen in component step b1), example 3 the removal in component step b2).

Example 1

A membrane-electrode assembly with an active area of 5 $cm^2$ was used, which had a membrane based on phosphoric acid-filled polybenzimidazole. This membrane is obtainable under the Celtec P® name from BASF Fuel Cell GmbH. Gas diffusion electrodes obtainable under the ELAT® name, likewise from BASF Fuel Cell GmbH, were used both for the anode and the cathode. Both the anode and the cathode comprised 1 $mg/cm^2$ of platinum. The experiments were performed at operating temperature 160° C. and at atmospheric pressure. The gas mixture was premixed for the separation tests and comprised 11.40 mol % of hydrogen, 88.10 mol % of methane, 5000 mol ppm of ethene, 100 mol ppm of benzene and 50 mol ppm of ethane. At different gas flow rates kept constant in each case on the anode side, the voltage was varied. The gas mixture obtained on the permeate side was analyzed by gas chromatography and the current densities were measured. Tables 1 and 2 show the hydrogen conversions and current densities achieved, the $H_2$ conversion referring to the amount of $H_2$ removed in % based on the hydrogen present in the anode gas stream.

TABLE 1

| Flow rate | $H_2$ conversion [%] | | |
|---|---|---|---|
| [ml/min] | U = 200 mV | U = 400 mV | U = 600 mV |
| 100 | 82 | 88 | 87 |
| 200 | 60 | 79 | 75 |
| 300 | 50 | 69 | 70 |
| 500 | 33 | 50 | 52 |
| 1000 | 17 | 26 | 31 |

TABLE 2

| Flow rate | Current density [A/cm$^2$] | | |
|---|---|---|---|
| [ml/min] | U = 200 mV | U = 400 mV | U = 600 mV |
| 100 | 0.50 | 0.52 | 0.50 |
| 200 | 0.86 | 0.80 | 0.88 |
| 300 | 0.74 | 0.98 | 0.98 |
| 500 | 0.82 | 1.18 | 1.28 |
| 1000 | 0.86 | 1.30 | 1.54 |

Example 2

The test parameters and test apparatuses are the same as in example 1, except that the cathode comprised 1 mg/cm$^2$ Pd instead of Pt. The results are shown in tables 3 and 4.

TABLE 3

| Flow rate | $H_2$ conversion [%] | | |
|---|---|---|---|
| [ml/min] | U = 200 mV | U = 400 mV | U = 600 mV |
| 100 | 84 | 93 | 92 |
| 200 | 61 | 77 | 77 |
| 300 | 47 | 71 | 65 |
| 500 | 26 | 39 | 41 |
| 1000 | 8 | 14 | 18 |

TABLE 4

| Flow rate | Current density [A/cm$^2$] | | |
|---|---|---|---|
| [ml/min] | U = 200 mV | U = 400 mV | U = 600 mV |
| 100 | 0.52 | 0.56 | 0.56 |
| 200 | 0.67 | 0.86 | 0.82 |
| 300 | 0.73 | 0.94 | 0.94 |
| 500 | 0.82 | 1.10 | 1.14 |
| 1000 | 0.84 | 1.20 | 1.30 |

Example 3

The test conditions were the same as in example 1, except that air was conducted along the cathode side and the gas mixture with the same flow rates in each case along the anode side, and no voltage was applied. At different gas flow rates kept constant in each case, the gas mixture obtained on the permeate side was analyzed by gas chromatography, and the current densities were measured. Table 5 shows the hydrogen conversions and current densities achieved, the $H_2$ conversion referring to the amount of $H_2$ removed in % based on the hydrogen present in the anode gas stream.

TABLE 5

| Anode flow rate [ml/min] | Current density [A/cm$^2$] | $H_2$ conversion [%] |
|---|---|---|
| 100 | 0.24 | 33 |
| 200 | 0.26 | 20 |
| 300 | 0.27 | 14 |
| 500 | 0.28 | 6 |
| 1000 | 0.29 | 0.2 |

The invention claimed is:

1. A process for converting at least one aliphatic hydrocarbon to at least one aromatic hydrocarbon, comprising:
   a) converting a reactant stream E to a product stream P in the presence of a catalyst under nonoxidative conditions, wherein the reactant stream E comprises the at least one aliphatic hydrocarbon comprising 1 to 4 carbon atoms and the product stream P comprises the at least one aromatic hydrocarbon and a hydrogen a); and
   b) electrochemically removing at least some of the hydrogen a) formed in the converting a) from the product stream P with a gas-tight membrane-electrode assembly comprising at least one selectively proton-conducting membrane and, on each side of the at least one selectively proton-conducting membrane, at least one electrode catalyst,
wherein:
   at least some of the hydrogen a) is oxidized to protons over an anode catalyst on a retentate side of the at least one selectively proton-conducting membrane; and
   the protons, after passing through the at least one selectively proton-conducting membrane, on a permeate side over a cathode catalyst, are partly, in
   b1) reduced to a hydrogen b1) by application of a voltage, and the hydrogen b1) is partly, in
   b2) reacted with oxygen to give water to generate electrical power, wherein the oxygen originates from an oxygen-comprising stream O, which is contacted with the permeate side of the at least one selectively proton-conducting membrane.

2. The process of claim 1, further comprising removing the at least one aromatic hydrocarbon from the product stream P, wherein the removing is performed:
   between the converting a) and the electrochemically removing b); or
   after the electrochemical removing b).

3. The process of claim 1, wherein the product stream P, after removal of at least some of the hydrogen a) and of the at least one aromatic hydrocarbon, is recycled into the process.

4. The process of claim 1, wherein at least a portion of the electrical power generated in b2) is applied as the voltage in b1).

5. The process of claim 1, wherein the voltage required to reduce the protons to the hydrogen b1) is generated by the electrical power of b2).

6. The process of claim 1, wherein the electrochemically removing at least some of the hydrogen b) is performed at a temperature range of 20 to 1200° C.

7. The process to of claim 1, wherein the oxygen-comprising stream O comprises at least 15 mol % of oxygen.

8. The process of claim 1, wherein the oxygen-comprising stream O comprises air.

9. The process of claim 1, wherein the electrochemical removing at least some of the hydrogen b) is performed at a pressure range of 0.5 to 10 bar.

10. The process of claim 1, wherein a pressure in the electrochemically removing of at least some of the hydrogen b) is the same on the retentate side and on the permeate side.

11. The process of claim 1, wherein the reducing to hydrogen b1) is performed at a voltage range of 0.05 to 2000 mV relative to a hydrogen reference electrode.

12. The process of claim 1, wherein the at least one selectively proton-conducting membrane comprises at least one membrane selected from the group consisting of a polymer membrane and a ceramic membrane.

13. The process of claim 1, wherein at least one electrode of the gas-tight membrane electrode assembly comprises at least one gas diffusion electrode.

14. The process of claim 1, wherein the reactant stream E comprises at least 50 mol % of methane.

15. The process of claim 1, wherein the reactant stream E originates from natural gas.

\* \* \* \* \*